US011491717B2

(12) United States Patent
Hangst et al.

(10) Patent No.: US 11,491,717 B2
(45) Date of Patent: Nov. 8, 2022

(54) METHOD FOR PRODUCING A ROBOT ELEMENT IN PARTICULAR A GRIPPER, BY MEANS OF 3D PRINTING

(71) Applicant: Hochschule Offenburg, Offenburg (DE)

(72) Inventors: Nikolai Hangst, Dunningen (DE); Stefan Junk, Saarbrücken (DE); Thomas Wendt, Simonswald (DE)

(73) Assignee: Hochschule Offenburg, Offenburg (DE)

(*) Notice: Subject to any disclaimer, the term of this patent is extended or adjusted under 35 U.S.C. 154(b) by 64 days.

(21) Appl. No.: 16/776,973

(22) Filed: Jan. 30, 2020

(65) Prior Publication Data

US 2020/0247044 A1  Aug. 6, 2020

(30) Foreign Application Priority Data

Feb. 6, 2019  (DE) .......................... 102019102913.9

(51) Int. Cl.
| | |
|---|---|
| *B29C 64/171* | (2017.01) |
| *B25J 15/08* | (2006.01) |
| *B25J 19/04* | (2006.01) |
| *B33Y 10/00* | (2015.01) |
| *B33Y 80/00* | (2015.01) |

(52) U.S. Cl.
CPC ............ *B29C 64/171* (2017.08); *B25J 15/08* (2013.01); *B25J 19/04* (2013.01); *B33Y 10/00* (2014.12); *B33Y 80/00* (2014.12)

(58) Field of Classification Search
None
See application file for complete search history.

(56) References Cited

U.S. PATENT DOCUMENTS

| | | | |
|---|---|---|---|
| 2009/0108605 A1 | 4/2009 | Fraunhofer-Gesellschaft | |
| 2013/0331949 A1 | 12/2013 | Dehoff et al. | |
| 2016/0009030 A1* | 1/2016 | Mark ..................... | B33Y 10/00 264/308 |

(Continued)

FOREIGN PATENT DOCUMENTS

| | | |
|---|---|---|
| DE | 102005046160 C5 | 3/2007 |
| JP | 2017528661 A | 9/2017 |
| WO | 2013030064 A1 | 3/2013 |

(Continued)

OTHER PUBLICATIONS

Vetani et al., Combined 3D Printing Technologies and Material for Fabrication of Tactile Sensors, International Journal of Precision Engineering and Manufacturing vol. 16, No. 7 (2015) (Year: 2015).*

(Continued)

*Primary Examiner* — Matthew J Daniels
*Assistant Examiner* — Paul Spiel
(74) *Attorney, Agent, or Firm* — The Culbertson Group, P.C.

(57) ABSTRACT

A method for 3D printing of a robot element, more particularly a finger for use in robotics. At least one sensor is concomitantly printed by means of multi-material printing during the printing of the robot element. A gripping element produced by a method of this kind includes a number of printed layers of robot element material and a concomitantly printed sensor.

9 Claims, 17 Drawing Sheets

(56) References Cited

U.S. PATENT DOCUMENTS

2016/0198576 A1     7/2016   Lewis et al.
2019/0047210 A1*   2/2019   Hussain .................. H01L 33/56

FOREIGN PATENT DOCUMENTS

WO       2016174242 A1    11/2016
WO       2020041221 A1     2/2020

OTHER PUBLICATIONS

Periard et al., "Printing Embedded Circuits," 2007 International Solid Freeform Fabrication Symposium, p. 503-512 (Year: 2007).*
Japanese patent application No. 2020016801A Japanese Office Action dated Jul. 26, 2021.

* cited by examiner

METHOD FOR PRODUCING A ROBOT ELEMENT IN PARTICULAR A GRIPPER, BY MEANS OF 3D PRINTING

TECHNICAL FIELD OF THE INVENTION

The invention relates to methods for producing a robot element, in particular a gripper, which may be used in a robotic system to grip, hold, or otherwise interact with an object such as a workpiece for example.

BACKGROUND OF THE INVENTION

Increasingly high requirements with expanding application profiles are being placed on gripping systems in robotics. Conventional types of production such as casting by means of appropriate molds, cutting methods, etc., only cover the fields of application in part, however, so that it is not only necessary to exchange gripping systems on a robot, which increases the set-up time, but also that several different gripping systems must be produced correspondingly.

SUMMARY OF THE INVENTION

The present invention addresses the problem of creating a method for producing a robot element, in particular a gripper, which method is multi-functionally applicable and reduces the set-up time of a robot.

By virtue of the fact that an entire robot element (for gripping, actuating, moving, etc.) such as gripping or actuating fingers, jaws, etc., is produced by means of 3D printing, additional manufacturing processes that are normally required, such as attaching separate sensors and coating with (usually flexible) materials, are unnecessary.

According to the invention, a robot element of this type is produced by means of multi-material printing so that not only special, usually flexible, outer surfaces or layers of a gripping or actuating element can be flexibly designed, but also at least one sensor (capacitive, inductive, resistive, Hall-effect) can be integrated during the production of the robot element, more particularly during the printing of the robot element, i.e. the sensor itself is produced by means of printing.

In addition, the production process according to the invention offers the possibility of ensuring a required load-carrying capacity, tear resistance, bending strength, rigidity, hardness, etc., by appropriate selection of material, particularly for the lower or inner layers of the gripping or actuating element, wherein different materials can be used to produce different layers. In this manner, desired different material properties can be integrated into one and the same element or component in a single production process, without requiring further machining steps.

In a preferred embodiment of the invention, a combination of multiple (identical or different) sensors are concomitantly printed during the printing of the robot element. This makes redundant and/or multifunctional sensor systems possible, without the necessity for subsequent machining of a component produced according to the invention.

In a further embodiment of the invention, terminals, lines, plugs and/or connecting elements are concomitantly printed, without requiring subsequent machining of a component produced according to the invention.

In a particularly preferred embodiment of the invention, composite material, particularly fiber reinforcement, is concomitantly printed (microfibers) or embedded (continuous fibers) during printing. For example, very short fiber constituents, so-called microfibers (especially carbon fibers, polyamide, etc.) can already be present in the printing material and applied in this way (concomitantly printed) by means of a nozzle to the printing bed or the already existing layers. In addition, the fiber can also be inserted as a continuous fiber (especially a carbon fiber), with the aid of a second nozzle, into any desired layer during the printing or during a printing pause.

In a further embodiment of the invention, sensors and fiber reinforcement are distributed during the printing onto different layers. This can prevent conductive fiber reinforcements from impairing sensors or even producing short-circuits. It is also possible for an insulating layer to be provided at a transition between a layer or layers containing sensors and layers having electrically conductive fibers so that an (electrical) functional impairment of a sensor can be excluded.

In a further embodiment of the invention, at least one camera is integrated by insertion/embedding during printing (possibly also during a pause before printing the next layer).

In a particularly advantageous embodiment of the invention, an entire actuating or gripping element, more particularly fingers and possibly including joint elements, of a robot is printed by means of multi-material printing in a single (printed) piece.

The weight in comparison to conventional gripping systems or actuating systems can advantageously be reduced by the above-mentioned embodiments, because elements such as sensors, leads, plugs, connecting elements, etc., are concomitantly printed and/or embedded. The fiber reinforcement by means of 3D multi-material printing according to the invention also contributes to reducing the weight by achieving a higher load carrying capacity, tear resistance, bending strength, rigidity, hardness, etc., of the material by means of the above-mentioned fiber reinforcement rather than by increasing the quantity of material. In addition, bionic shapes can be achieved by the method according to the invention in a simple manner, i.e. material is only used where it is needed, for reasons of strength, for example.

These and other advantages and features of the invention will be apparent from the following description of representative embodiments, considered along with the accompanying drawings.

DESCRIPTION OF REPRESENTATIVE EMBODIMENTS

Figure 1:
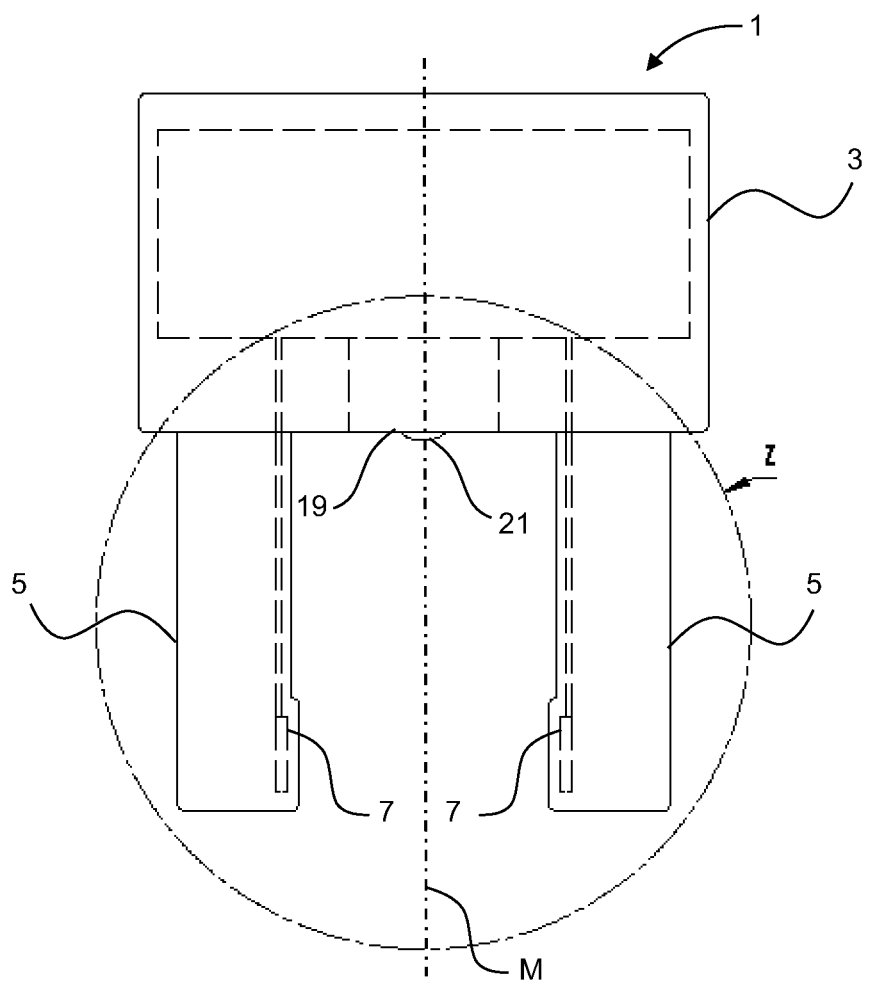
FIG. 1 is a front view of a schematic representation of a gripping system produced according to the invention for a robot.
Figure 2:
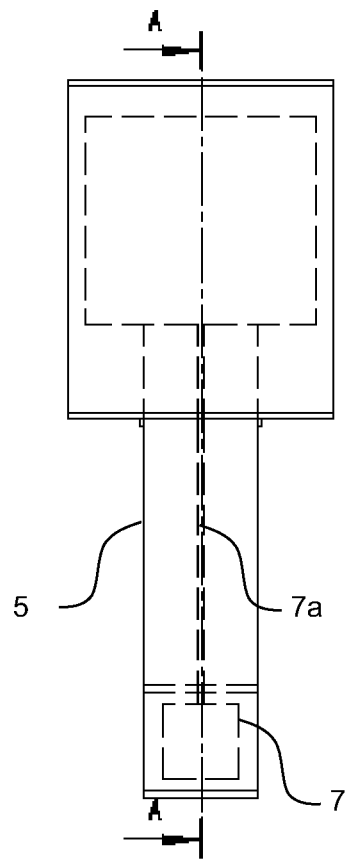
FIG. 2 is a side view of the gripping system shown in FIG. 1.
Figure 3:
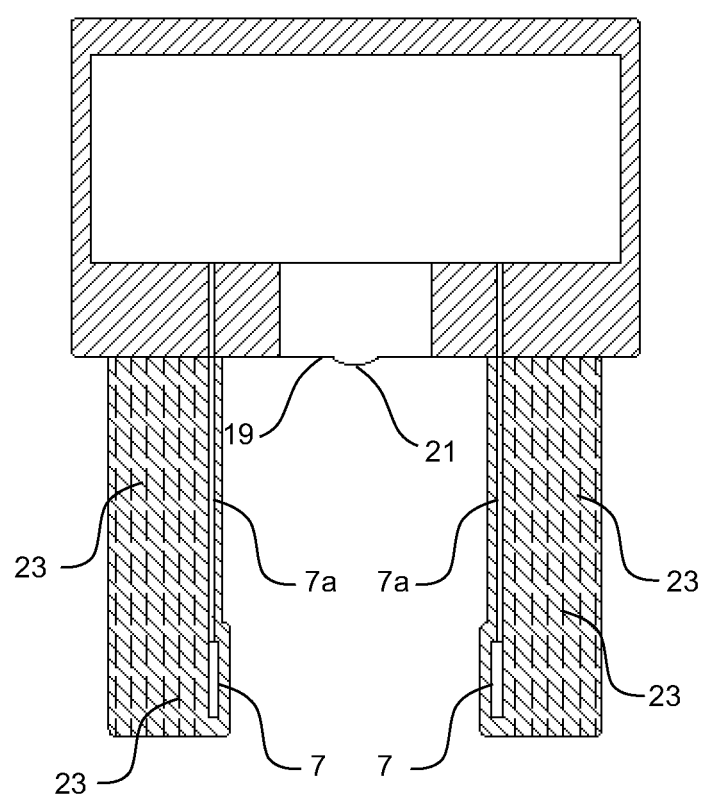
FIG. 3 is a sectional view along section line A-A in FIG. 2.
Figure 4:
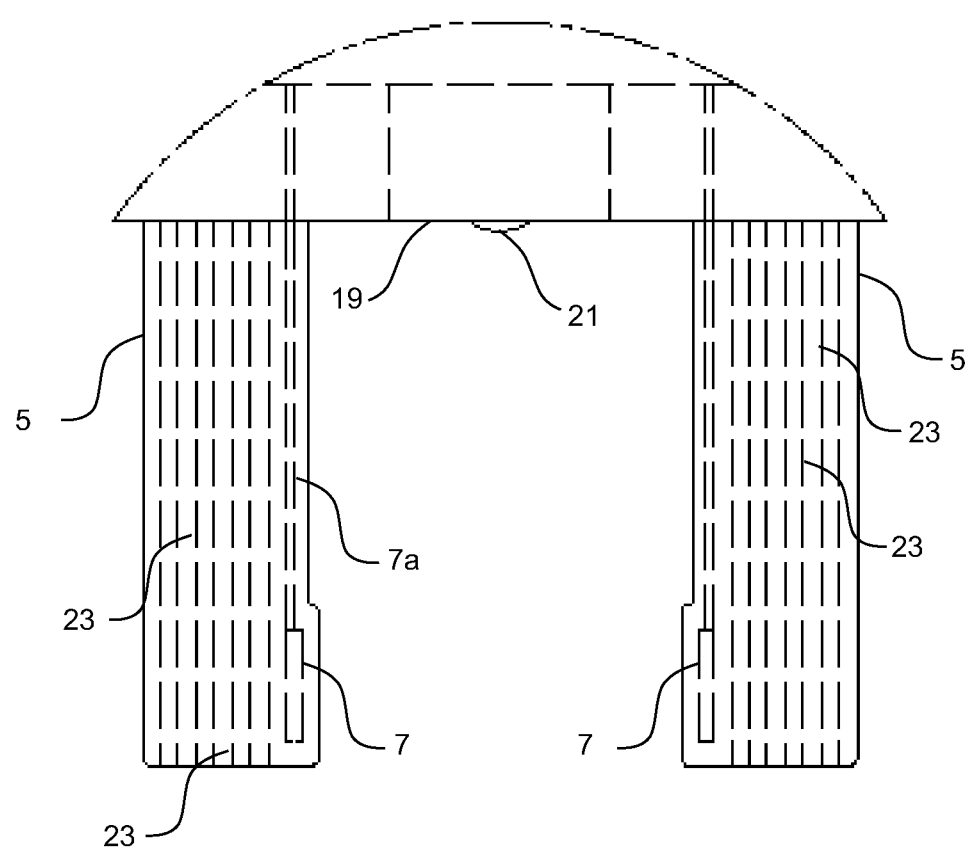
FIG. 4 is an enlarged view of detail Z in FIG. 1.

The gripping system 1 illustrated in FIGS. 1-4 for a robot includes a control unit 3 and multiple, for example two, gripping elements or actuating elements constructed as fingers 5. The control unit 3 constitutes the mechanical link between the fingers 5 and the robot, and preferably also establishes an electrical connection between the two components. The structure forming each finger 5 is preferably provided with an actuator of its own in order to guarantee any desired rotation of the fingers 5 and fast removal and modification thereof. In addition, the fingers can preferably be inclined—by 7° for example—with respect to the longitudinal axis of the respective finger in order to enable a reduction of the gripping distance or the gripping time for different objects.

For gripping, the fingers 5, preferably designed rotationally symmetrically relative to the central axis M of the gripping system 1, can be moved along an axis transverse to the central axis of the gripping system 1 (horizontally in the drawing plane of FIG. 1) between a maximum separation relative to one another (as shown in the drawing) and a minimum separation (up to mutual contact of the fingers).

It goes without saying that the illustrated gripping system 1 having two fingers 5 serves only as an example for general gripping systems according to the invention, and gripping systems having multiple fingers, such as three fingers distributed equally about the central axis M, are also conceivable.

The rotation, tilting and movement of the fingers 5 can be implemented by an appropriate device (in particular electrical actuating motors) in the region of the connection between the control unit 3 and the fingers 5, or in the fingers 5 themselves (for example, in different finger segments or additionally present finger joints).

The two fingers 5 shown in FIGS. 1-4, that is, the gripping element structures represented by the two fingers 5 have sensors 7 (shown schematically in FIGS. 1-4) on the inner side thereof, which are integrated (by means of multi-material printing) into one of the upper layers or in the uppermost layer in the direction of the central axis M, and are preferably located underneath the outermost layer, which functions as an outer skin. In this manner, the sensors 7 are protected from external mechanical contact. Capacitive, resistive and inductive sensors as well as Hall sensors can be considered as sensor types in this regard.

The sensors 7 have supply lines 7a (leads or terminals) which, like the sensors 7, are also printed inside the fingers 5 and lead to the control system or to the electronics accommodated therein. If necessary, the sensors 7 can be accessible, in a manner not shown in further detail, from the exterior via the supply lines 7a thereof by means of corresponding connecting elements (plugs, bushings, etc.), and can be connected to corresponding terminals of a robot. The connecting elements can also be concomitantly printed or embedded.

The sensor 7, constructed in different ways (capacitor, coil, resistor, strain gauges, Hall sensor, etc.), is preferably coplanar within a layer (the uppermost of the outer layers for example), which is itself constructed as an electrically insulating layer.

Below or also above this layer having a sensor 7, it is also possible for fiber reinforcements 23 (by microfibers in the printing material or by inserting endless fibers into the printing bed) to be present, even if the fiber reinforcements include electrically conductive material (e.g. carbon).

In the center region between the fingers 5, a camera 19 is embedded in the control unit 3, the object lens 21 of which is directed in the direction of the fingers 5 or of an object to be gripped thereby and covers the region between the fingers 5 in order to visually detect an object to be gripped or actuated.

The camera 19 can be embedded during a printing pause by inserting it into a printed recess, or a positioned camera can be enclosed by printing such that the lens or objective thereof is situated at a desired point and has a desired focus.

The connecting lines (terminals) and connecting elements for connecting the camera can advantageously be concomitantly printed or also embedded, so that the camera need not be contacted externally or via external surfaces. An integrated design of this type contributes to reducing the installation height and avoiding undesired external cable bushings.

Different embodiments of the sensor 7 shown in general in FIGS. 1-4 are described below in connection with FIGS. 5-21.

Figure 5:
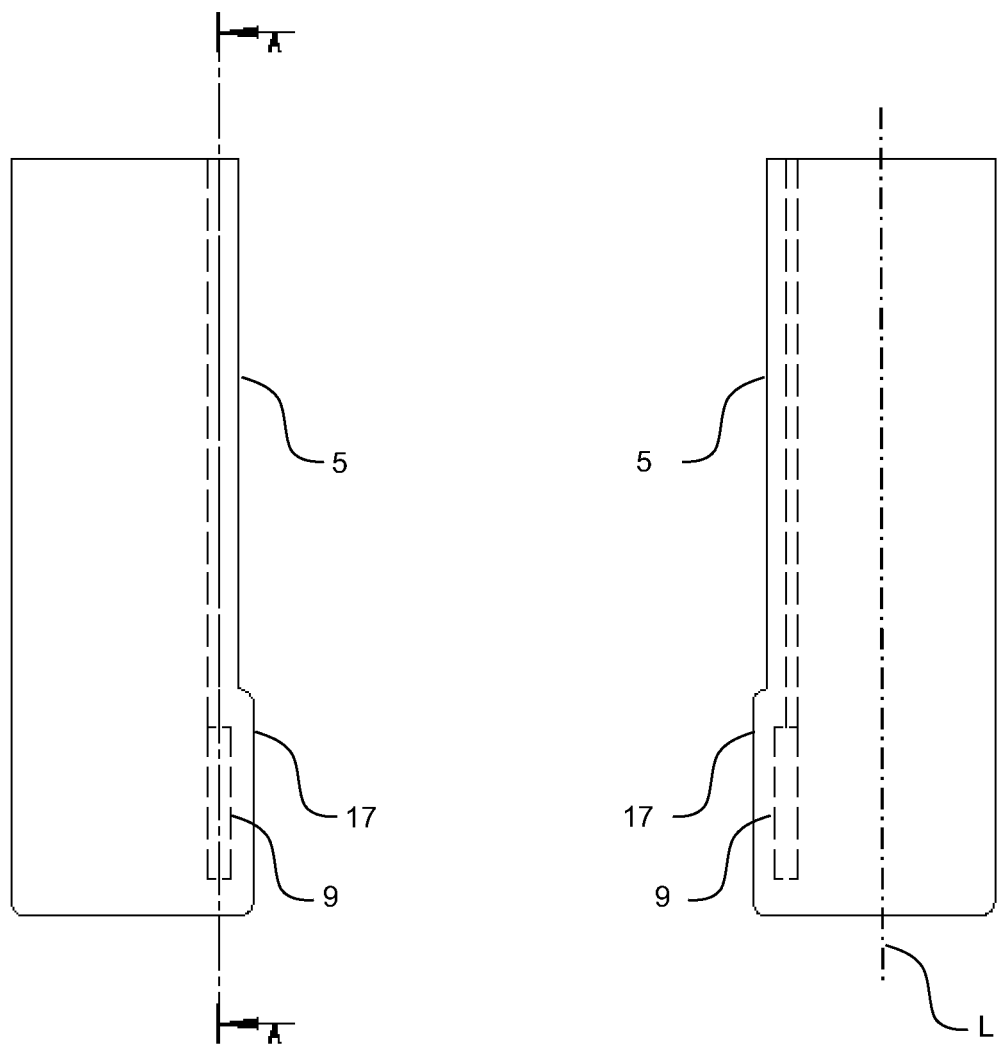
FIG. 5 is a front view of the gripping fingers from FIGS. 1-4 with capacitive sensors.
Figure 6:
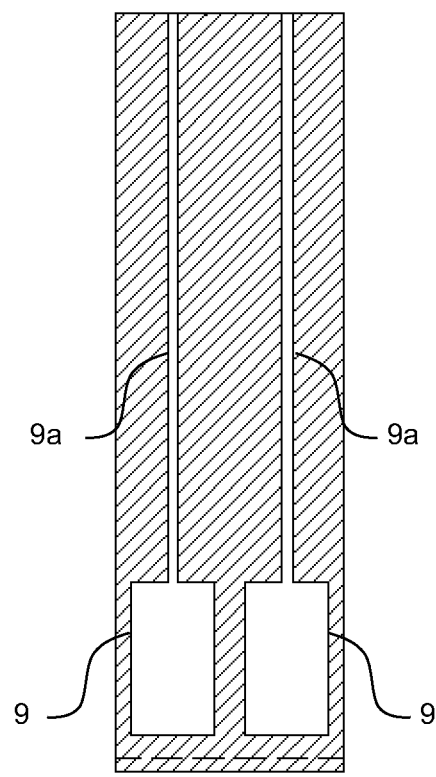
FIG. 6 is a sectional view of the gripping finger along line A-A in FIG. 5.

In a first embodiment, the fingers 5 shown as a detail in FIGS. 5 and 6 have capacitive sensors 9 with supply lines 9a in the end regions thereof or in the gripping surfaces of the fingertips. As is evident from FIG. 5, the two plates of the sensors 9 lie horizontally one next to another in the drawing plane, although an arrangement one above another (vertically in the drawing plane) is of course also conceivable. The two plates of the capacitive sensor (capacitor) implemented in this manner are coplanar in the same (external) layer, which also serves as insulation (dielectric) between the plates.

Figure 7:
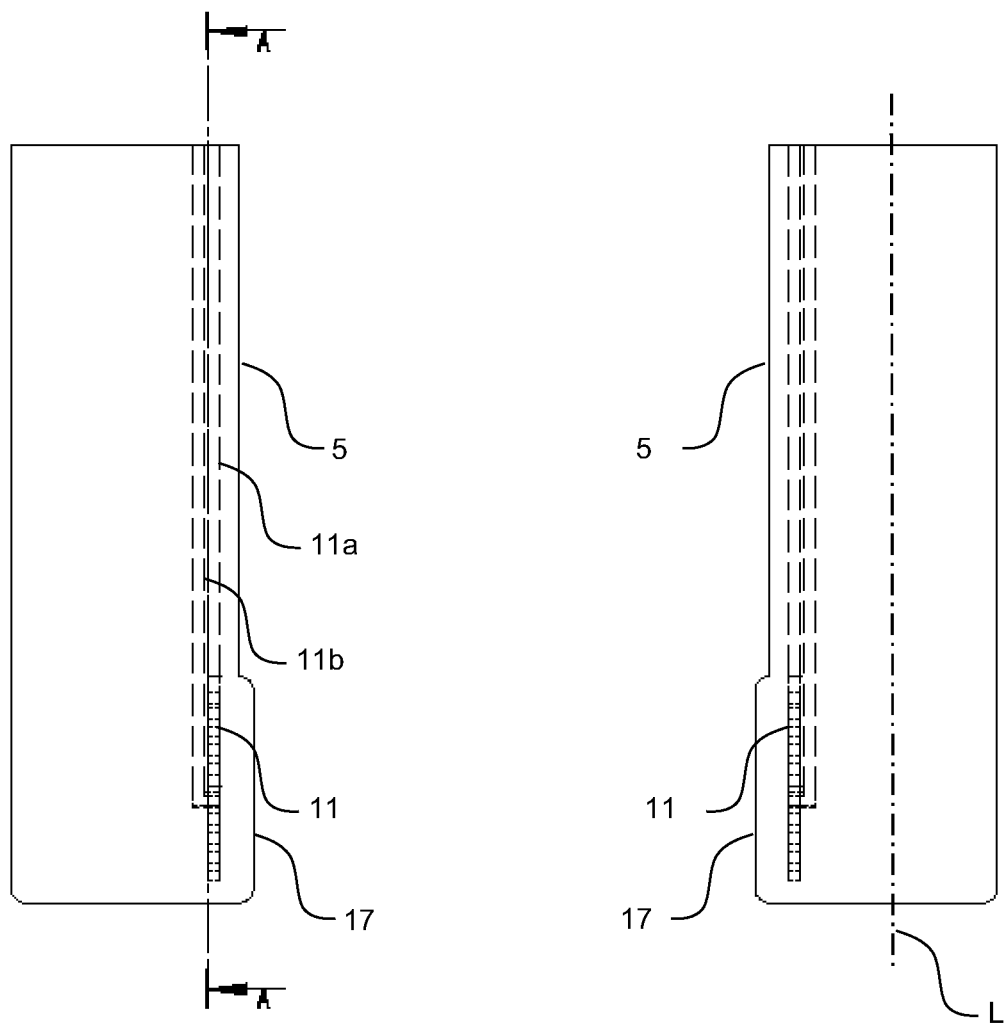
FIG. 7 is a front view of the gripping fingers from FIGS. 1-4 with inductive sensors.
Figure 8:
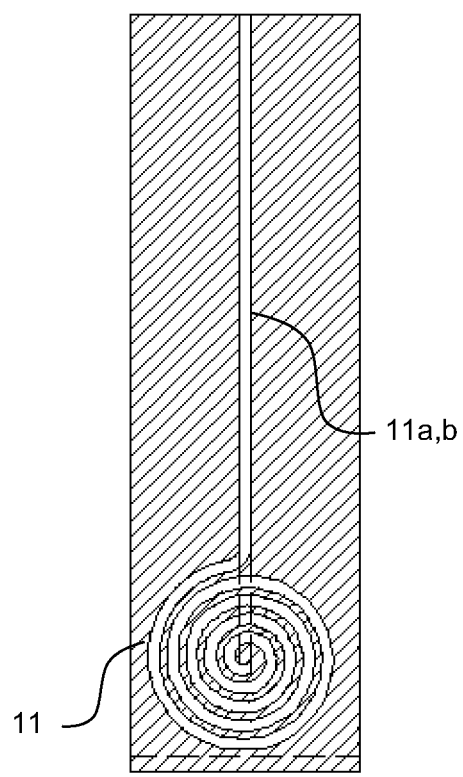
FIG. 8 is a sectional view of the gripping finger along line A-A in FIG. 7.

In the second embodiment, presented in FIGS. 7 and 8, the fingers 5 have coils 11 located in a layer (coplanar with the layer plane) as inductive sensors (rather than capacitive sensors 9) with supply lines 11a (end tap) and 11b (center tap). The layer shown in a plan view is any type of layer that can be inductively influenced. In order to increase the sensitivity of the sensor, this layer is preferably one of the upper layers or even the outermost layer of the finger.

Figure 9:
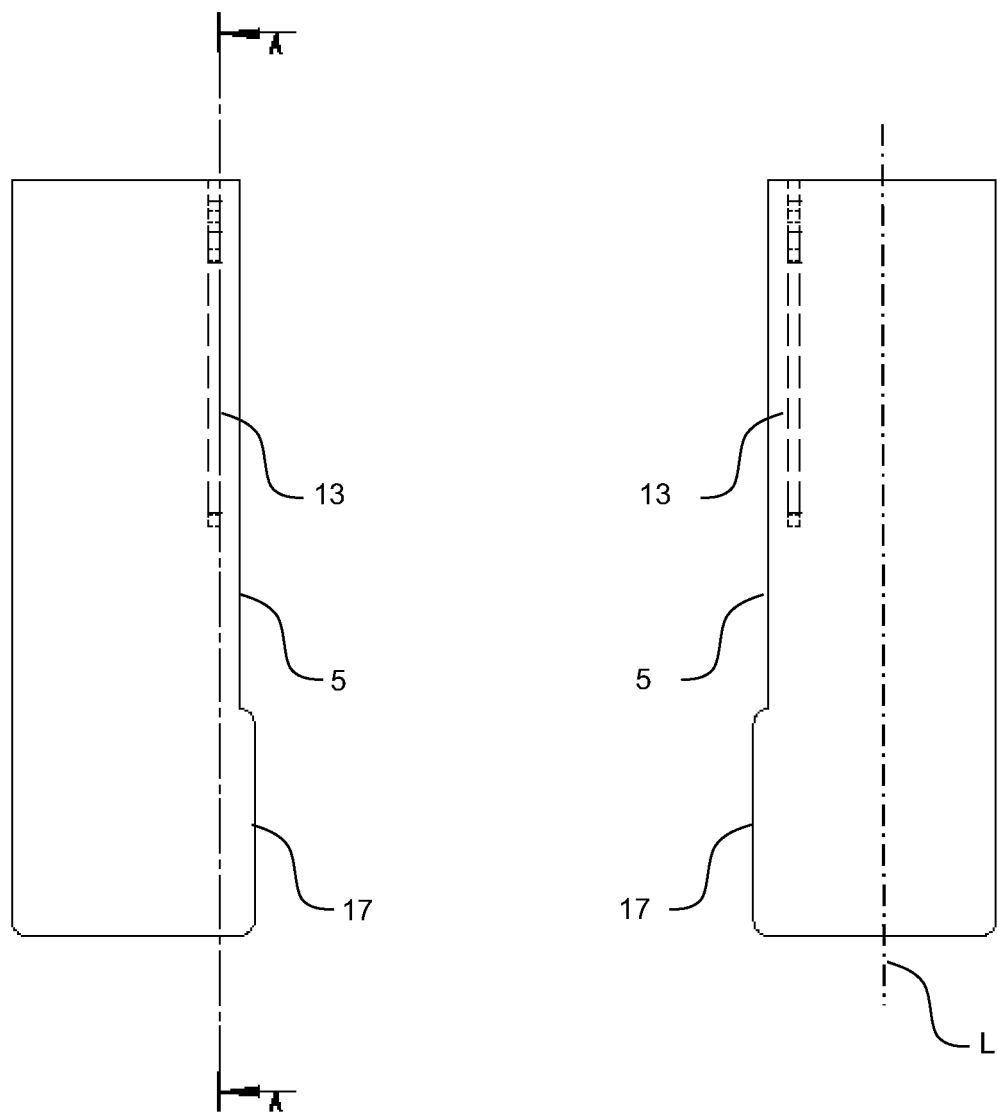
FIG. 9 is a front view of the gripping fingers from FIGS. 1-4 with resistive sensors.
Figure 10:
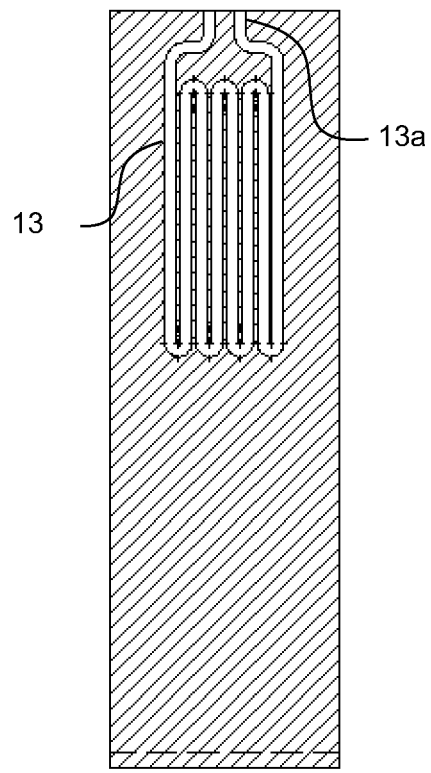
FIG. 10 is a sectional view of the gripping finger along line A-A in FIG. 9.
Figure 11:
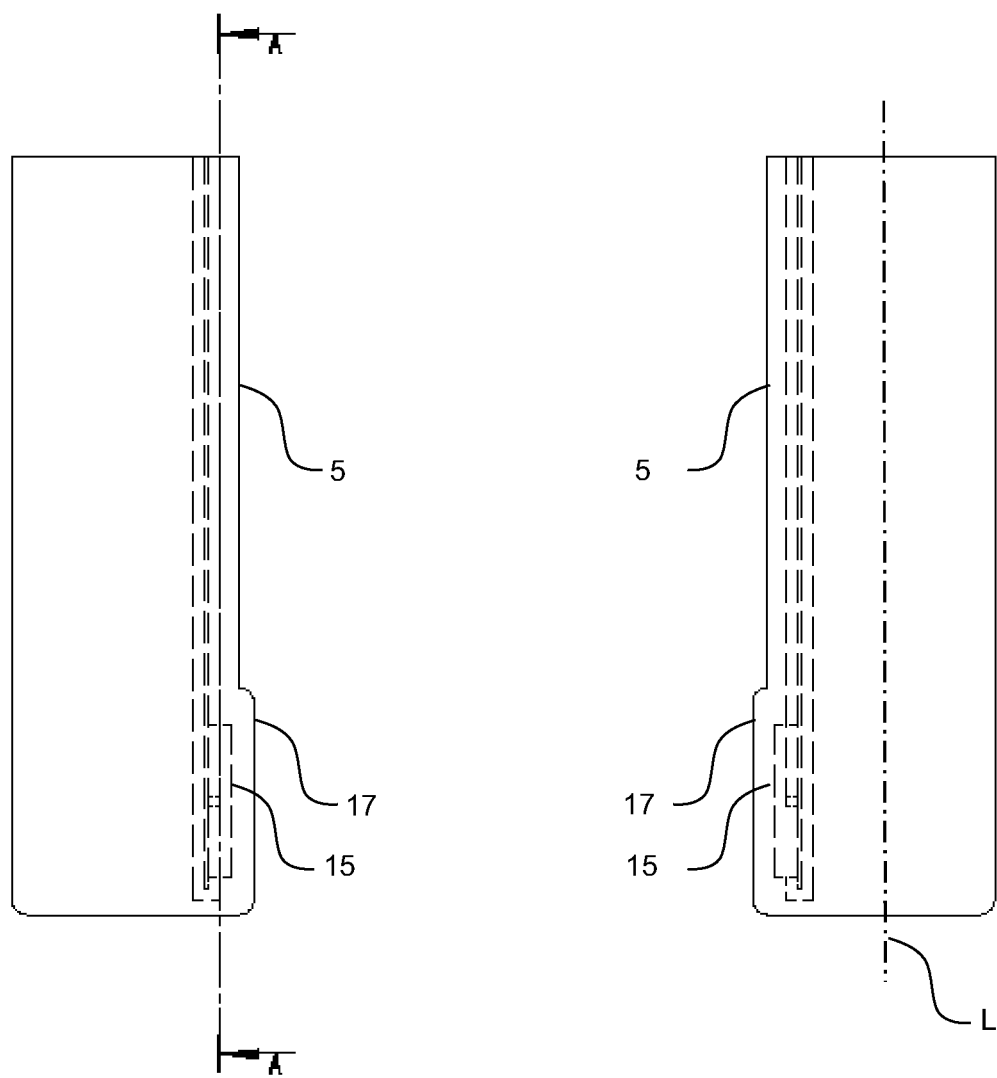
FIG. 11 is a front view of the gripping fingers from FIGS. 1-4 with Hall sensors.
Figure 12:
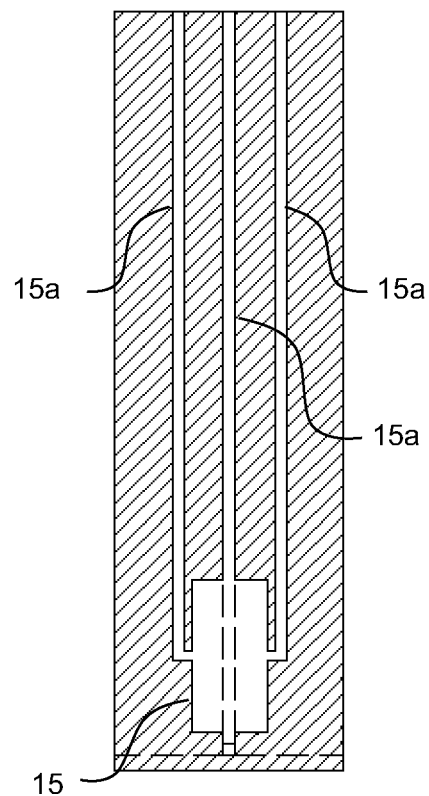
FIG. 12 is a sectional view of the gripping finger along line A-A in FIG. 11.

In a manner analogous to FIGS. 7 and 8, the third embodiment, presented in FIGS. 9 and 10, features strain gauges 13 (resistive sensors) rather than coils 11, the strain gauges being printed coplanar with supply lines 13a in one plane, wherein the layer shown here can also be any type of layer that is influenced mechanically, and need not be the outermost layer. The strain gauge 13 preferably has a greater extent (length) in the direction of the longitudinal axis L of the finger 5 than a width transversely to the longitudinal axis L, so that changes in length due to bending of the finger 5 under a load can be more easily detected.

The fourth embodiment, presented in FIGS. 11 and 12 FIGS. 5a and 5b, shows how—in a manner analogous to FIGS. 9 and 10—Hall sensors 15, rather than strain gauges 13, are printed coplanar with supply lines 15a, 15b and 15c in one plane, wherein the illustrated layer can be any type of layer that is influenced magnetically (inductively in this case), and need not necessarily be the outermost layer.

Figure 13:
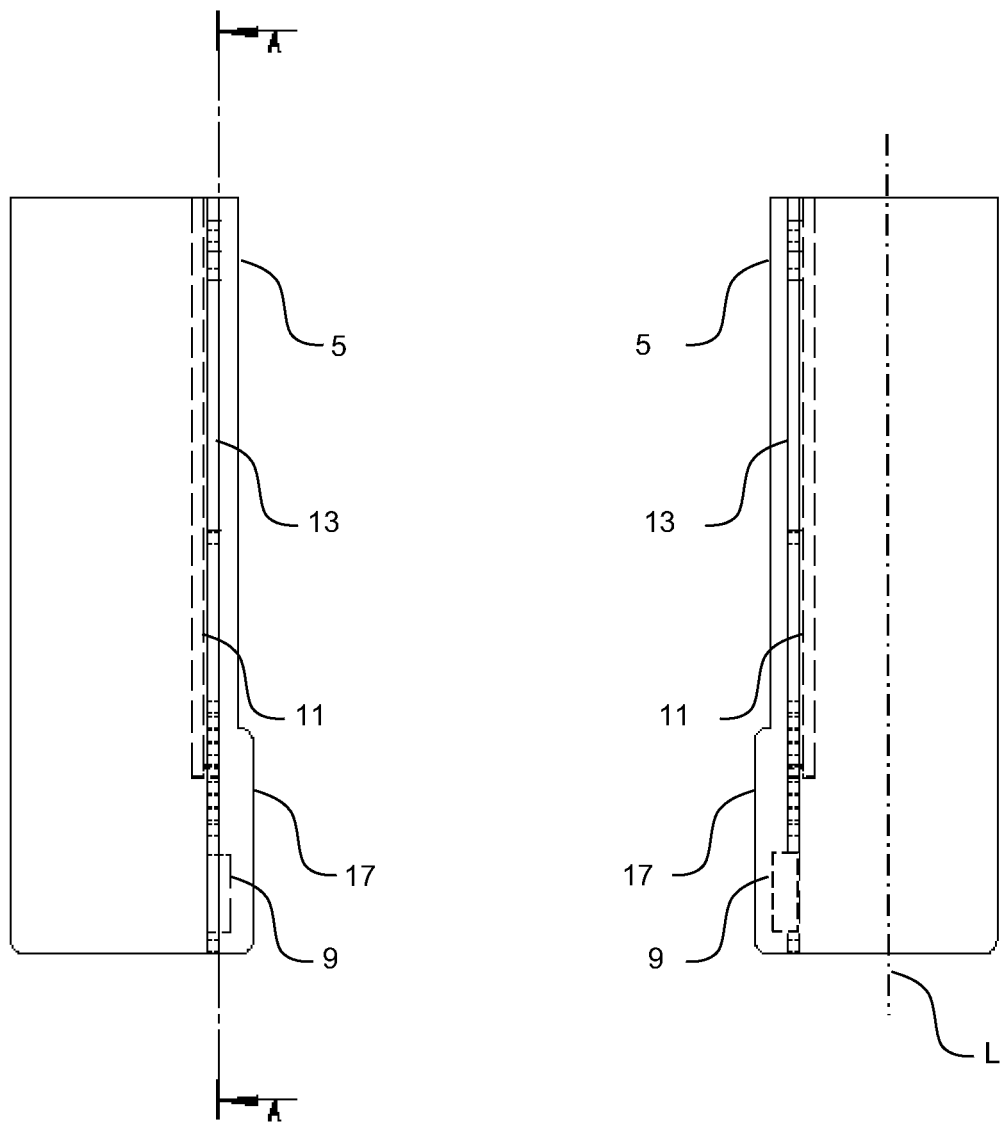
FIG. 13 is a front view of the gripping fingers from FIGS. 1-4 with a combination of capacitive, inductive and resistive sensors.
Figure 14:
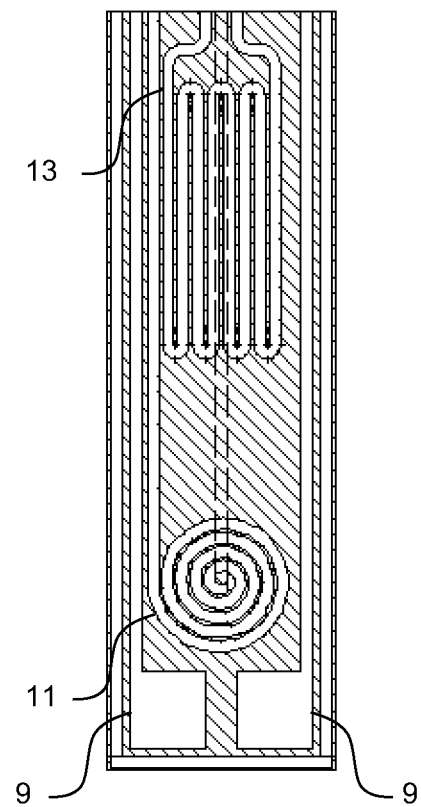
FIG. 14 is a sectional view of the gripping finger along line A-A in FIG. 13.
Figure 15:
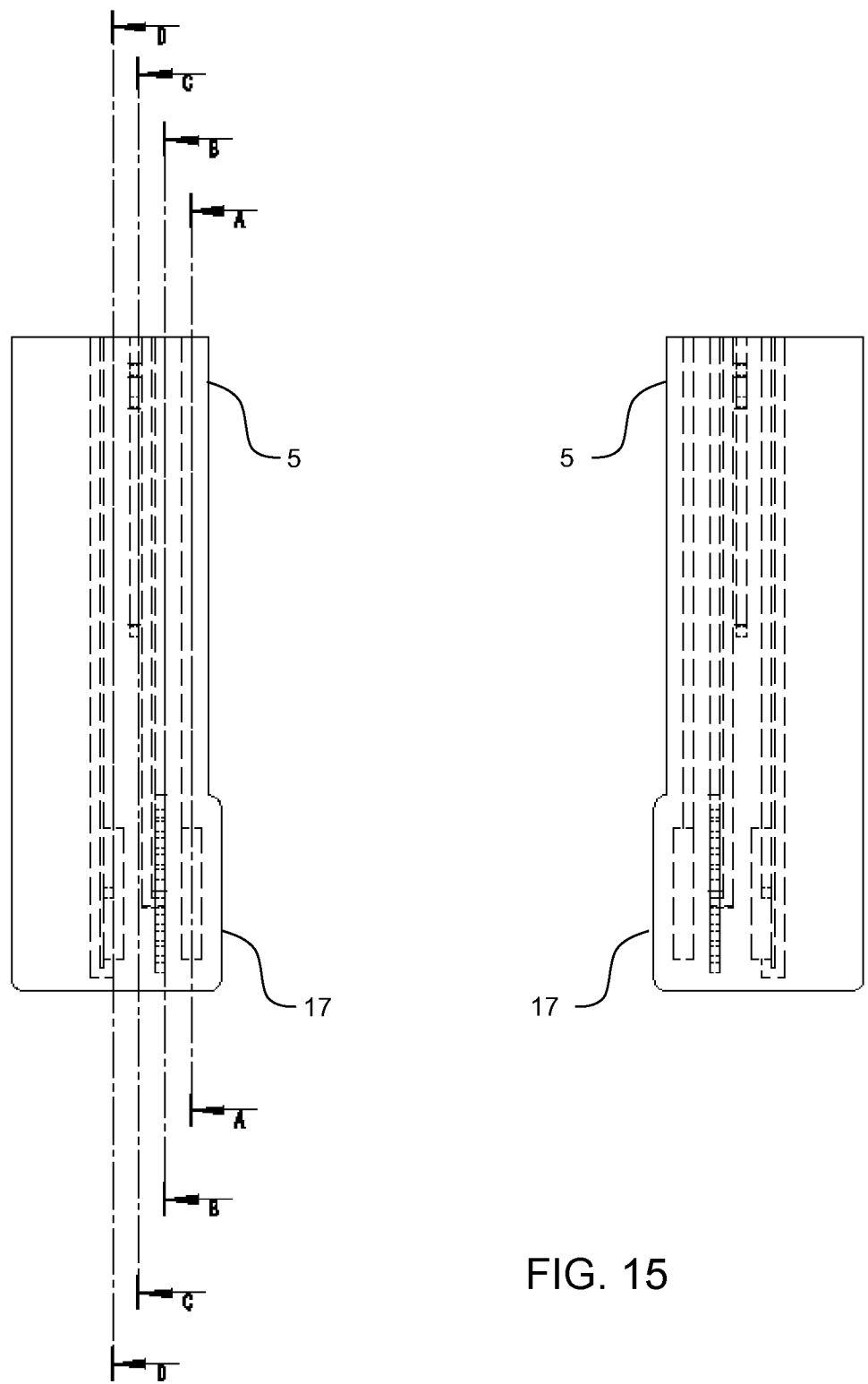
FIG. 15 is a front view of the gripping fingers from FIGS. 1-4 with capacitive, inductive, resistive and Hall sensors, each in different layers.

It is evident from the fifth embodiment, shown in FIGS. 13 and 14, that a combination of multiple sensors, namely a capacitive sensor 9, an inductive sensor 11 and a resistive sensor 13, can be printed within one layer.

Figures 16, 17, 18, 19:
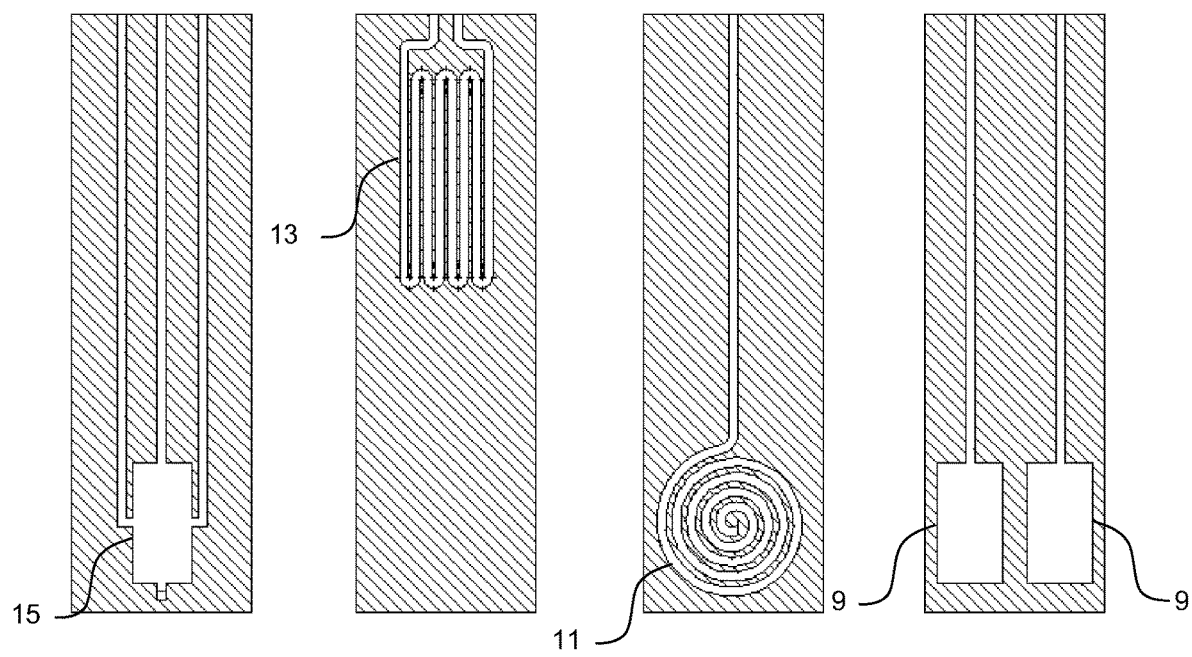
FIG. 16 is a sectional view of the gripping finger along line A-A in FIG. 15.
FIG. 17 is a sectional view of the gripping finger along line B-B in FIG. 15.
FIG. 18 is a sectional view of the gripping finger along line C-C in FIG. 15.
FIG. 19 is a sectional view of the gripping finger along line D-D in FIG. 15.

Instead of printing multiple identical or also different sensors 9, 11, 13, 15 as well as arbitrary combinations thereof within one layer, it is also possible, as shown in the sixth embodiment evident from FIGS. 15-19, to distribute the sensors 9, 11, 13, 15 over different layers. Instead of the two plates of a capacitive sensor 9 being arranged horizontally next to one another in the drawing plane, as shown in FIG. 16 (section A-A) it is of course possible for the plates to be arranged vertically one above another or offset from one another. The circular, schematic shape of the coil 11 shown in section B-B is only an example for any desired helical, particularly angular shape.

Due to the layer-by-layer structure of a multi-material print (3D), it is also possible to combine different carrier materials. For example, harder carrier materials can be used in layers remote from gripping surfaces (perpendicular to the longitudinal finger axis L) in order to increase the stability of a gripping element, more particularly a finger 5. In the area of the gripping surfaces 17, on the other hand, particularly in the end regions (fingertips), it is possible to use soft, elastic material such as rubber for the printing of an outer layer (and possibly for layers thereunder as well) in order to increase the friction between the finger 5 and the object and to reduce damage to an object to be gripped.

Figure 20:
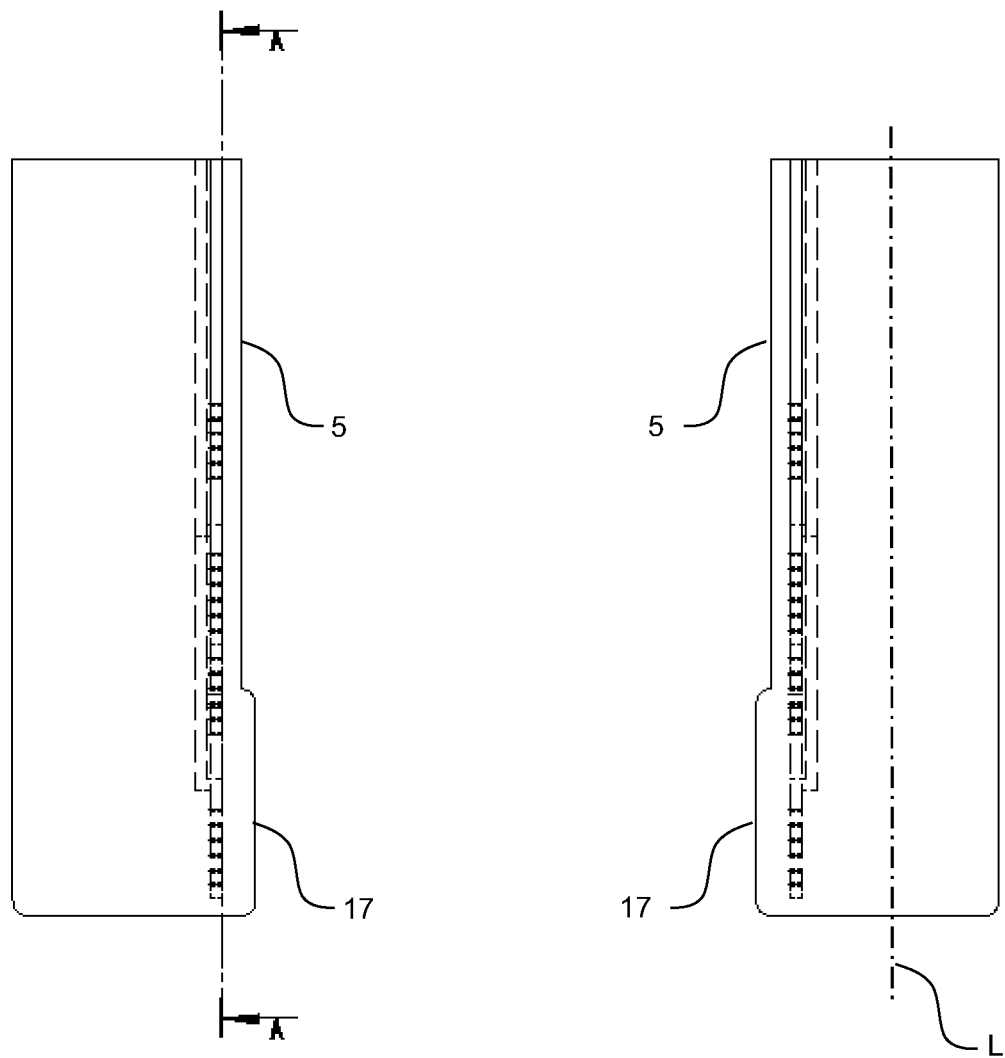
FIG. 20 is a front view of the gripping fingers from FIGS. 1-4 with multi-sensors.
Figure 21:
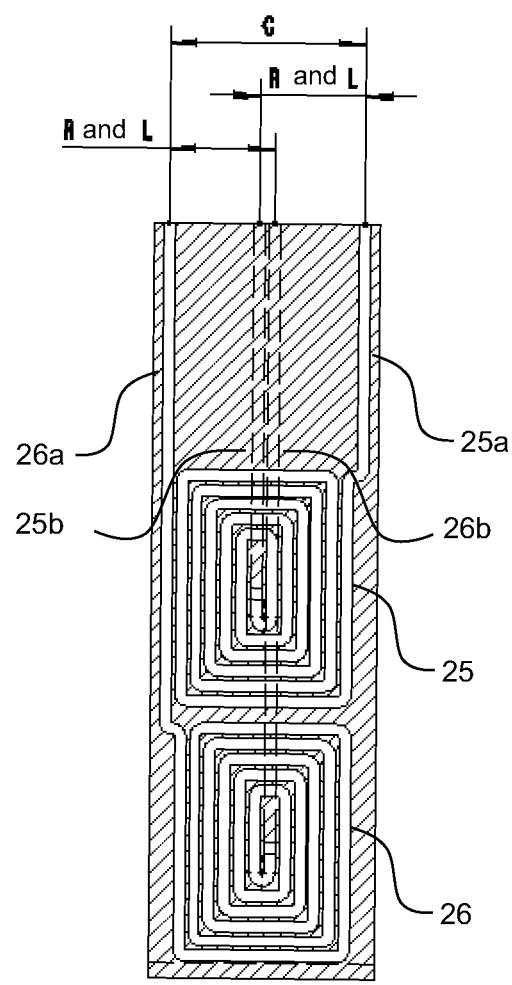
FIG. 21 is a sectional view of the gripping finger along line A-A in FIG. 20.

The sixth embodiment, shown in FIGS. 20 and 21, shows a multi-sensor, more particularly a 4-in-1 sensor having two rectangular spirals 25 (first multi-sensor element) and 26 (second multi-sensor element) arranged one below the other in the drawing plane. This multi-sensor can be operated as an inductive, capacitive or resistive sensor (strain gauge), depending on how the spirals 25 and 26 are connected via their terminals 25a, 25b and 26a, 26b.

If the two terminals (serving as end taps) 25a and 26a (or 25b and 26b) are used, then the multi-sensor functions as a capacitive sensor C as indicated in FIG. 21, the two sensor elements 25 and 26 serving as capacitor plates.

If only the outer and inner terminals or taps 25a and 25b, or 26a and 26b, are used, each sensor element 25 and 26 functions as a resistive sensor R or an inductive sensor L as indicated in FIG. 21. Rather than a double formation of the sensors, it is naturally also conceivable to connect the sensor elements in series, so that the sensor elements act as an enlarged inductive or resistive sensor.

If the sensor elements 25 and 26 act as two sensors, the two measured values obtained can be used for cross-checking (simple redundancy) or for eliminating disruptive factors (for example, eliminating the influence of heating in a measurement result).

As used herein, whether in the above description or the following claims, the terms "comprising," "including," "carrying," "having," "containing," "involving," and the like are to be understood to be open-ended, that is, to mean including but not limited to. Also, it should be understood that the terms "about," "substantially," and like terms used herein when referring to a dimension or characteristic of a component indicate that the described dimension/characteristic is not a strict boundary or parameter and does not exclude variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Any use of ordinal terms such as "first," "second," "third," etc., in the following claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The term "each" may be used in the following claims for convenience in describing characteristics or features of multiple elements, and any such use of the term "each" is in the inclusive sense unless specifically stated otherwise. For example, if a claim defines two or more elements as "each" having a characteristic or feature, the use of the term "each" is not intended to exclude from the claim scope a situation having a third one of the elements which does not have the defined characteristic or feature.

The above described preferred embodiments are intended to illustrate the principles of the invention, but not to limit the scope of the invention. Various other embodiments and modifications to these preferred embodiments may be made by those skilled in the art without departing from the scope of the present invention. For example, in some instances, one or more features disclosed in connection with one embodiment can be used alone or in combination with one or more features of one or more other embodiments. More generally, the various features described herein may be used in any working combination.

LIST OF REFERENCE NUMBERS

1 Gripping system
3 Control unit
5 Finger
7 Sensor
7a Supply line of sensor 7
9 Capacitor plates or capacitive sensor
9a Supply line of sensor 9
11 Coils or inductive sensor
11a Supply line of sensor 11 outer terminal (end tap)
11b Supply line of sensor 11 inner terminal (center tap)
13 Strain gauge or resistive sensor
13a Sensor supply line
15 Hall sensors
15a Sensor supply line
17 Gripping surface
19 Camera
21 Objective
23 Fiber reinforcement
25 First multi-sensor element
25a Supply line for the outer terminal (end tap) of sensor 25

25*b* Supply line for the inner terminal (end tap) of sensor 25
26 Second multi-sensor element
26*a* Supply line outer terminal (end tap) of sensor 26
26*b* Supply line for the inner terminal (end tap) of sensor 26
M Central axis of the gripping system 1
L Longitudinal axis of finger 5
Z Detail

The invention claimed is:

1. A method for producing a gripping element for a robot, the method including:
   (a) printing a number of layers of gripping element material with a multi-material 3D printing system to form a gripping element structure wherein the gripping element structure comprises part of a gripping system;
   (b) concomitantly with forming the gripping element structure, printing at least one additional component of the gripping system;
   (c) concomitantly with forming the gripping element structure, printing a sensor of the gripping element with the multi-material 3D printing system into a first one of the number of layers of the gripping element material so the sensor is integrated with the gripping element structure, the sensor being printed with a sensor material different from the gripping element material; and
   (d) embedding at least one camera into the gripping system concomitantly with printing the number of layers of the gripping element material.

2. The method of claim 1 further including, concomitantly with forming the gripping element structure, printing at least one additional sensor of the gripping element with the multi-material 3D printing system, the at least one additional sensor being printed with an additional sensor material different from the gripping element material and the additional sensor material being printed into the first one of the layers of the gripping element material or a second one of the layers of the gripping element material different from the first one of the layers of the gripping element material.

3. The method of claim 1 further including, concomitantly with forming the gripping element structure, printing at least one terminal for the sensor with the multi-material 3D printing system, the at least one terminal for the sensor being printed into one of the number of layers of the gripping element material with terminal material different from the gripping element material.

4. The method of claim 1 further including, concomitantly with forming the gripping element structure, printing at least one lead for the sensor with the multi-material 3D printing system, the at least one lead for the sensor being printed into one of the number of layers of the gripping element material with lead material different from the gripping element material.

5. The method of claim 1 further including, concomitantly with forming the gripping element structure, printing at least one connecting element for the sensor with the multi-material 3D printing system, the at least one connecting element for the sensor being printed into one of the number of layers of the gripping element material with connecting element material different from the gripping element material.

6. The method of claim 1 further including, concomitantly with forming the gripping element structure, placing a fiber reinforcement material within the layers of the gripping element material, the fiber reinforcement material being placed by printing with the multi-material 3D printing system or by embedding.

7. The method of claim 6 wherein the sensor material and fiber reinforcement material are distributed during printing into different layers of the gripping element.

8. The method of claim 1 wherein the gripping element comprises a finger of the gripping system and the finger is printed in one piece.

9. The method of claim 1 wherein printing the number of layers of the gripping element material includes printing an outer layer of gripping element material over the printed sensor material so that the printed sensor material does not form an outermost layer of the gripping element.

\* \* \* \* \*